(12) United States Patent
Cappellaro et al.

(10) Patent No.: US 9,417,068 B2
(45) Date of Patent: Aug. 16, 2016

(54) STABLE THREE-AXIS NUCLEAR SPIN GYROSCOPE

(71) Applicants: Paola Cappellaro, Somerville, MA (US); Ashok Ajoy, Cambridge, MA (US)

(72) Inventors: Paola Cappellaro, Somerville, MA (US); Ashok Ajoy, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 734 days.

(21) Appl. No.: 13/874,718

(22) Filed: May 1, 2013

(65) Prior Publication Data

US 2014/0327439 A1 Nov. 6, 2014

(51) Int. Cl.
*G01C 19/62* (2006.01)
*G01N 24/08* (2006.01)

(52) U.S. Cl.
CPC .............. *G01C 19/62* (2013.01); *G01N 24/08* (2013.01)

(58) Field of Classification Search
CPC ................................ G01C 19/62; G01N 24/08
See application file for complete search history.

(56) References Cited

U.S. PATENT DOCUMENTS

| | | | | |
|---|---|---|---|---|
| 2,551,180 A * | 5/1951 | Starr | ......................... | H01Q 1/18 324/123 R |
| 4,219,775 A * | 8/1980 | Bozanic | ................. | G01R 33/60 324/310 |
| 4,326,803 A * | 4/1982 | Lawrence | ............ | G01C 19/727 356/461 |
| 7,898,356 B2 * | 3/2011 | Sherrer | ..................... | H01P 3/06 29/828 |
| 7,902,530 B1 * | 3/2011 | Sahadevan | ........... | A61N 5/1042 250/341.7 |
| 8,542,079 B2 * | 9/2013 | Sherrer | ..................... | H01P 3/06 333/260 |
| 8,547,090 B2 * | 10/2013 | Lukin | .................. | G01R 33/032 324/244.1 |
| 9,000,863 B2 * | 4/2015 | Sherrer | ..................... | H01P 3/06 29/828 |
| 2010/0308813 A1 | 12/2010 | Lukin et al. | | |
| 2010/0315079 A1 | 12/2010 | Lukin et al. | | |
| 2014/0340085 A1 * | 11/2014 | Cappellaro | ............ | G01R 33/60 324/316 |

OTHER PUBLICATIONS

Ledbetter et al., "Gyroscopes based on nitrogen-vacancy centers in diamond" Physical Review A 86, 052116, Nov. 19, 2012, pp. 052116-1-052116-5.
D. Le Sage et al., "Efficient photon detection from color centers in a diamond optical waveguide" Physical Review B 85, 121202(R), Mar. 23m, 2012, pp. 121202-1-121202-4.
MacLaurin et al., "Large adiabatic geometric phase in rotating single atom-scale diamond defects" The Australian Research Council Centre of Excellence for Quantum Computation and Communication Technology, arXiv:1202.3472v1 [quatntum-ph], Feb. 15, 2012, pp. 1-5.
Ledbetter et al., "Gyroscopes based on nitrogen-vacancy centers in diamond" arXiv:1205.0093v1 [physics.atom-ph] May 1, 2012, pp. 1-5.

* cited by examiner

*Primary Examiner* — Dixomara Vargas
(74) *Attorney, Agent, or Firm* — Gesmer Updegrove LLP

(57) ABSTRACT

An n-NV-based gyroscope is provided that includes a diamond structure implanted with a plurality of NV centers, whose nuclear spins form a spin gyroscope. A number of radio-frequency (rf) coils and microwave (µw) co-planar waveguides are fabricated on the diamond structure to provide a sensitive and stable three-axis gyroscope in the solid state while achieving gyroscopic sensitivity by exploiting the coherence time of the $^{14}$N nuclear spin associated with the NV centers in the diamond structure combined with the efficient optical polarization and measurement of electronic spin.

33 Claims, 5 Drawing Sheets

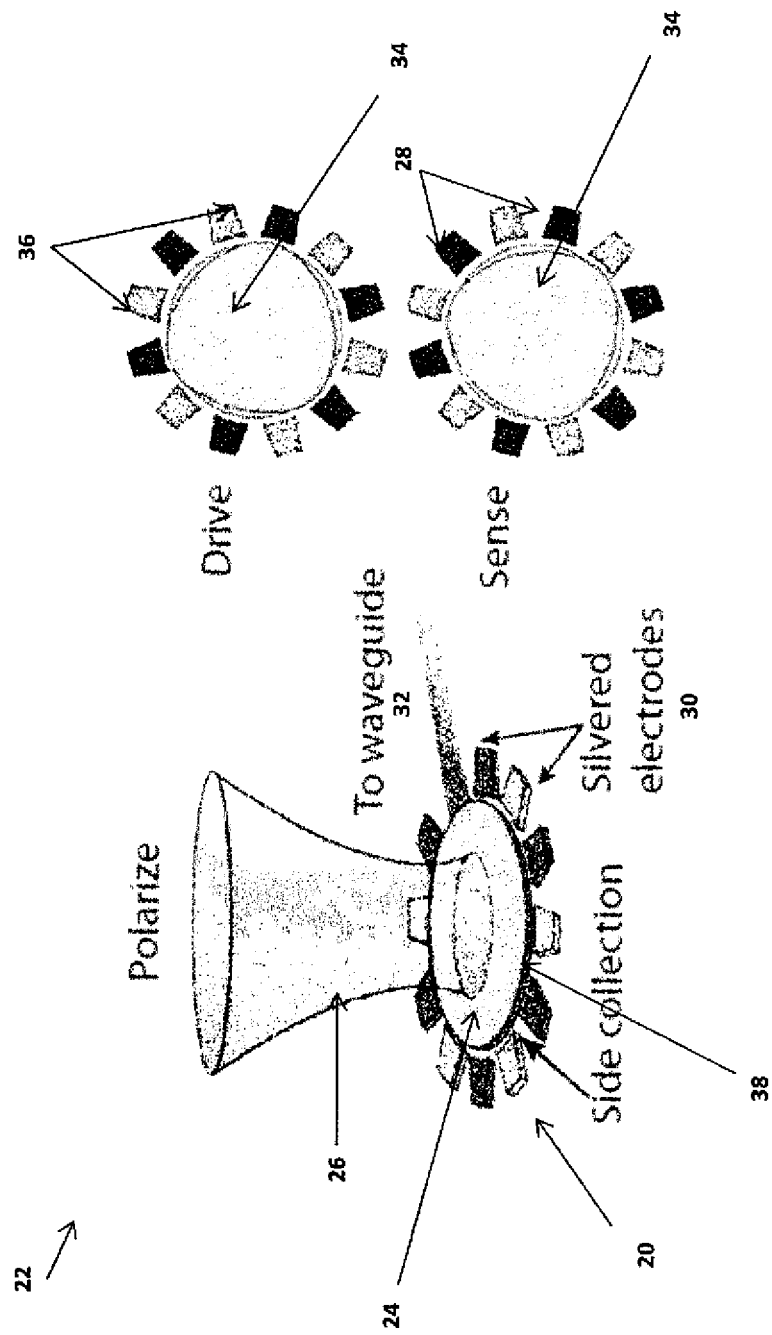

STABLE THREE-AXIS NUCLEAR SPIN GYROSCOPE

SPONSORSHIP INFORMATION

This invention was made with government support under Contract No. W911NF-11-1-0400 awarded by the Army Research Office. The government has certain rights in the invention

BACKGROUND OF THE INVENTION

The invention related to the field of gyroscopes, and in particular a quantum-based gyroscope that provides a sensitive and stable three-axis gyroscope in the solid state.

Conventional commercial gyroscopes are built using microelectromechanical systems (MEMS) technology that allows for sensitivities exceeding 3 (mdeg s$^{-1}$)/$\sqrt{Hz}$ in a hundreds of micron-sized footprint. Despite several advantages—including low current drives (~100 μA) and large bandwidths (200 deg/s)—that have allowed MEMS gyroscopes to gain ubiquitous usage, they suffer from one critical drawback: The sensitivity drifts after a few minutes of operation, making them unattractive for geodetic applications. The intrinsic reason for these drifts formation of charged asperities at the surface of the capacitive transduction mechanism is endemic to MEMS but does not occur in other systems used as gyroscopes, such as atom interferometers or nuclear spins. However, to achieve sensitivities comparable to MEMS, these systems require large volumes (~cm$^3$), long startup times, and large power and space overheads for excitation and detection.

SUMMARY OF THE INVENTION

According to one aspect of the invention, there is provided an n-NV-based gyroscope. The n-NV-based gyroscope includes a diamond structure implanted with a plurality of Nitrogen-Vacancy defect color centers in diamond (NV centers), whose nuclear spins form a spin gyroscope. A number of radio-frequency (rf) coils and microwave (μw) co-planar waveguides are fabricated on the diamond structure to provide a sensitive and stable three-axis gyroscope in the solid state while achieving gyroscopic sensitivity by exploiting the coherence time of the $^{14}$N nuclear spin associated with the NV centers in the diamond structure combined with the efficient optical polarization and measurement of electronic spin.

According to another aspect of the invention, there is provided a method of implementing a quantum sensor. The method includes implanting a plurality of NV centers in a diamond structure, whose nuclear spins form a spin gyroscope. Moreover, the method includes fabricating a plurality of radio-frequency (rf) coils and microwave (μw) co-planar waveguides on the diamond structure to provide a sensitive and stable three-axis gyroscope in the solid state while achieving gyroscopic sensitivity by exploiting the coherence time of the $^{14}$N nuclear spin associated with the NV centers in the diamond structure combined with the efficient optical polarization and measurement of electronic spin.

According to another aspect of the invention, there is provided a quantum sensor. The quantum sensor includes a diamond structure implanted with a plurality of NV centers, whose nuclear spins form a spin gyroscope. A number of radio-frequency (rf) coils and microwave (μw) co-planar waveguides are fabricated on the diamond structure to provide a sensitive and stable three-axis gyroscope in the solid state while achieving gyroscopic sensitivity by exploiting the coherence time of the $^{14}$N nuclear spin associated with the NV centers in the diamond structure combined with the efficient optical polarization and measurement of electronic spin.

BRIEF DESCRIPTION OF THE DRAWINGS

FIGS. 5A-5B are schematic diagrams illustrating an integrated n-NV-MEMS gyroscope.

DETAILED DESCRIPTION OF THE INVENTION

The invention overcomes the drawbacks of current gyroscopes by using a solid-state spin associated with the nuclear spin of nitrogen-vacancy (NV) centers in diamond as a gyroscope (referred herein as n-NV gyro). The n-NV gyro combines the efficient optical initialization and measurement offered by the NV-electronic spin with the stability and long coherence time of the nuclear spin, which is preserved even at high densities.

Figure 1:
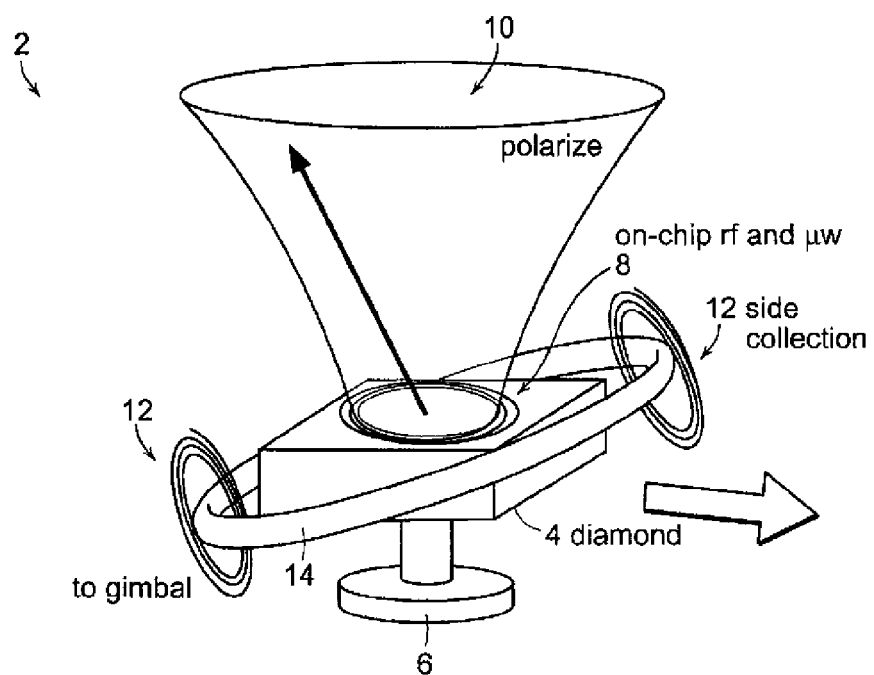
FIG. 1 is a schematic diagram illustrating an n-NV gyroscope formed in accordance with the invention.

FIG. 1 is a schematic diagram illustrating a n-NV gyro 2 formed in accordance with the invention. A slab of diamond 4 of dimensions (2.5×2.5) mm2×150 μm is anchored to the device body 6. Radio-frequency (rf) coils and microwave (μw) co-planar waveguides 8 are fabricated on the diamond 4 for fast control. NV centers are polarized by a green laser (532 nm) 10, and state dependent fluorescence intensity (637 nm) is collected employing a side-collection technique. A second set of rf coils 12 rotate with respect to the diamond-chip frame, for example, by being attached to one or more rings 14 in a mechanical gimbal gyroscope. The $^{14}$N nuclear spins are used as probes of the relative rotation between the diamond frame and the external rf-coil frame.

The operating principles are based on the detection of the phase that the nitrogen-14 nuclear spin 1 ($^{14}$N) acquires when it rotates around its symmetry axis. Consider an isolated spin 1 with Hamiltonian $H_0 = QI_z^2 + \gamma_N bI_z$, where Q is the intrinsic quadrupolar interaction (Q=−4.95 MHz for the NV center's $^{14}$N), b is a small magnetic field, $\gamma_N b \ll Q$, and $\gamma_N = 2\pi \times 3.1$ MHz/T is the $^{14}$N gyromagnetic ratio. The spin is subject to rf fields in the transverse plane at frequency Q and with a (gated) amplitude $2\omega_{rf}(t)$. The diamond rotates around the spin-symmetry axis (z axis) at a rate Ω with respect to the frame in which the rf field is applied. Thus, the driving field is described by the Hamiltonian $H_{rf} = 2\omega_{rf}(t)\cos(Qt)[I_x \cos(\Omega t) - I_y \sin(\Omega t)]$. One can describe the spin evolution in the interaction frame set by $(QI_z^2 - \Omega I_z)$. The second term ($e^{-i\Omega I_z}$) transforms $H_{rf}$ to $$2\omega_{rf}\cos(Qt)I_x = \omega_{rf}[e^{-iQI_z^2 t}I_x e^{iQI_z^2 t} + e^{iQI_z^2 t}I_x e^{-iQI_z^2 t}] \quad (1)$$

Figure 2:
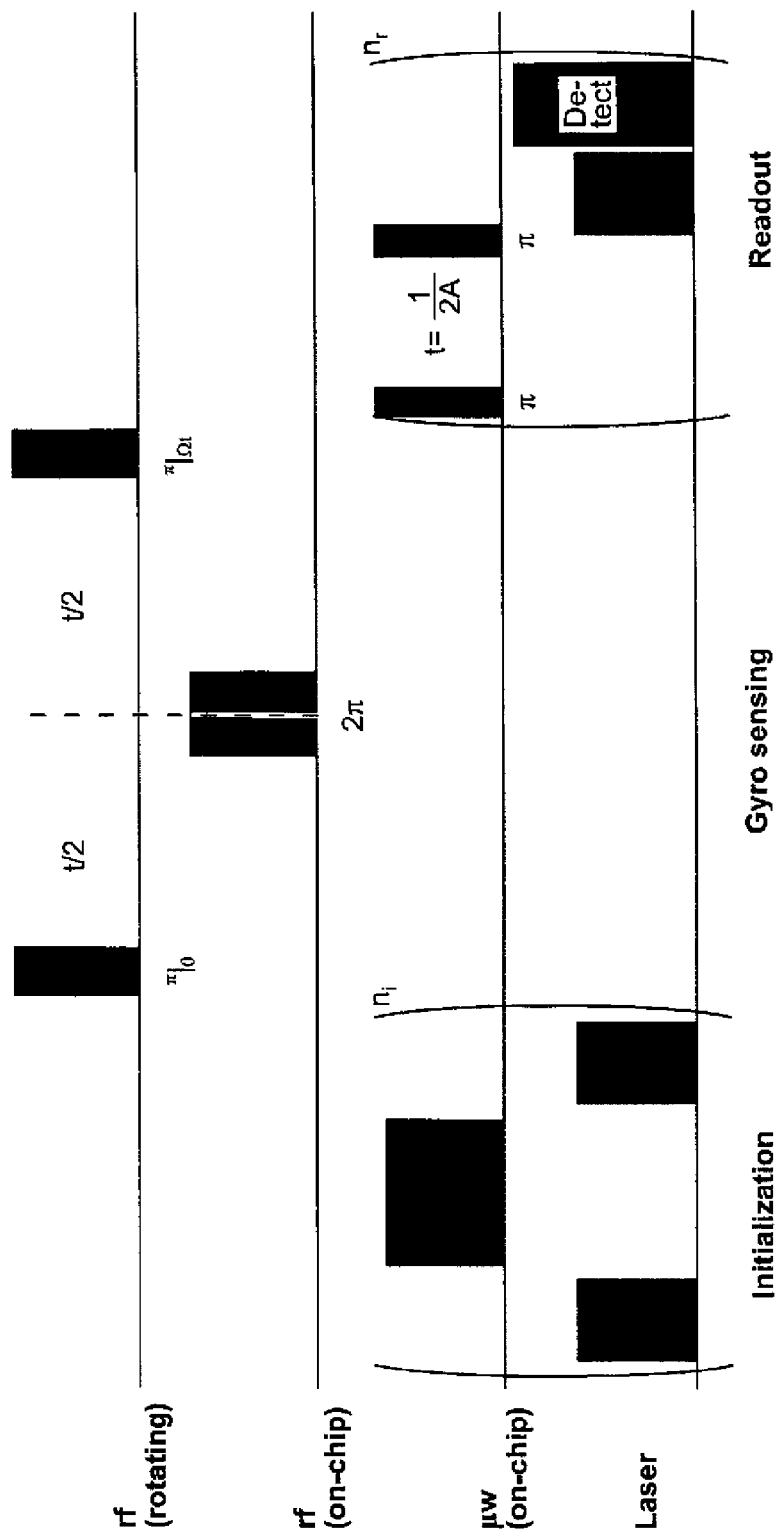
FIG. 2 is a graph illustrating an n-NV-gyroscope control sequence.

In a Ramsey sequence shown in FIG. 2, the spin acquires a phase $\phi = (\gamma_N b + \Omega)t$ from which one can extract the rotation rate. Although the n-NV-gyro operating principles are somewhat similar to NV-based magnetometers and NMR gyroscopes, some critical differences lead to its outstanding performance. In contrast to magnetometry, the sensitivity to rotation rates is independent of the spin's gyromagnetic ratio. Thus, one can exploit the $^{14}$N nuclear spin as a sensor, leading to a much improved performance because of the isolation of nuclear spins from noise sources. However, this also requires new strategies for the polarization and readout of the nuclear spin. There are two critical advantages of the n-NV gyro with respect to NMR gyros.

Although certain NMR-gyroscope designs use optical pumping for spin polarization the n-NV gyro exploits the unique properties of the NV electron spin for optical polarization and readout of the nuclear spins, achieving far better efficiencies, close to 100%. Furthermore, using a solid-state system allows the application of control fields in the same reference frame of the sensor spins, which, as shown below, decouple the spins from low-frequency noise sources, such as temperature fluctuations, stray magnetic fields, and strains. Stated equivalently, whereas NMR gyros are limited by the dephasing time $T^*_2$ the spins, the n-NV gyro is limited by the much longer coherence time $T_2$.

Consider first the operation of a one-axis n-NV gyro. The nuclear spin is first initialized by polarization transfer from the electronic NV spin. Under optical excitation, the electronic $ms=\pm 1$ levels follow a non-spin-preserving transition through metastable levels down to the $ms=0$ ground state, yielding high polarization of the electronic spin. The polarization can be transferred to the nuclear spin exploiting the hyperfine coupling $A=2.2$ MHz in the electron-nuclear-spin Hamiltonian, $$H_{en} = \Delta S_z^2 + \gamma_e b S_z + QI_z^2 + (\Omega + \gamma_N b)I_z + A\vec{S}\cdot\vec{I} \quad (2)$$

where $\gamma_e=2.8$ MHz/G is the electronic gyromagnetic ratio and $\Delta=2.87$ GHz is the zero-field splitting.

Several techniques for polarization transfer have been implemented experimentally, including measurement post selection and exploiting a level anticrossing in the orbital excited state at $b\sim500$ G (using an adiabatic passage or the resonance between the nuclear and the electronic spins). Unfortunately, all these techniques have drawbacks that make them unsuitable for purposes of the invention. The first technique is too lengthy, whereas the second prevents the use of repeated readouts and requires precise alignment of a large static magnetic field. At low field, polarization transfer between the electronic and the nuclear spins is complicated by the fact that both are spin 1.

Unlike for spin 1/2, polarization transfer in the rotating frame (under the Hartmann-Hahn-matching condition) does not lead to perfect polarization, unless the electronic spin is reduced to an effective spin 1/2. Instead, the invention proposes using forbidden two-photon transitions to achieve population transfer. Driving the NV-electronic spin at the $\Delta\pm\gamma_e b+Q$ transitions with a field along its longitudinal (z) axis modulates its resonance frequency, thus, making energy exchange with the nuclear spin possible.

Although the transition rates are usually small, the ability to drive the NV-electronic spin with very high fields makes the polarization time $$t = \pi\frac{\Delta + \gamma_e b + Q}{A\Omega_R}$$

short. For a Rabi frequency=500 MHz and a field $b=20$ G, the time required is only 1.3 μs. This initialization time is far shorter than for other gyroscope types, including the few tens of milliseconds of startup time required for MEMS gyroscopes.

For ease of operation, one can assume that the rf and μw pulses used for initialization and readout can be delivered by an on-chip circuit, integrated with the diamond. After preparation, the NV-electronic spin is left in the $|0\rangle$ state, which does not couple to the $^{14}$N nuclear spin nor to the spin bath. A Ramsey sequence is applied using the off-chip rf driving, thus, inducing accumulation of a rotation-dependent phase [Eq. (1)]. A $2\pi$ pulse at the center of the sequence, applied with the on-chip rf field, refocuses the effects of stray magnetic fields and provides decoupling from the spin bath. The sensor spin coherence time is limited by $T_2$ (and not by the shorter dephasing time $T^*_2$), which can be exceptionally long for nuclear spins. Thus, the additional pulse, made possible by working with a solid-state device, is critical in making the n-NV gyro immune to a host of low-frequency drifts that limit the operational time of other gyroscope types.

Moreover, since the echo refocuses the coupling to other electronic spins, the n-NV gyro can operate at very high densities of the sensor spins. Ion implantation can reach an NV density of n-NV$\sim 10^{18}$ cm$^{-3}$. Even assuming a density of residual single-nitrogen defects (P1 centers) $n_{P1}\approx 10$ n-NV$\sim 10^{19}$ cm$^{-3}$, the N $T_2$ time is not appreciably affected by the P1 bath. Indeed, while at these densities, the dipole-dipole interaction $$d_{ab} = \frac{\mu_0}{4\pi}\frac{\hbar}{2\pi}\frac{\gamma_a\gamma_b}{r_{ab}^3}$$

among P1 centers is large ($d_{P1,P1}\sim 3$ MHz with $\gamma_{P1}=\gamma_e$), and the coupling to the nuclear spin is still small, $d_{P1,N}\sim 345$ Hz (where the mean-spin-spin distance is estimated as $r=$ $$r = \sqrt[3]{\ln(8)/(4\pi\cdot n_{p1})}.$$

This leads to motional narrowing and a very slow exponential decay as confirmed by simulations.

The N coherence time is also affected by the interaction with the close-by NV center, which induces dephasing when undergoing relaxation with $T_1\sim 2-6$ ms at room temperature and low field. Whereas, in high-purity diamonds, the dephasing time $T^*_2$ can be as long as 7 ms, in the proposed conditions of operation, one can conservatively estimate the coherence time of the nuclear spin to be $T_2=1$ ms. The echo sequence has the added benefit to make the measurement insensitive to many other imperfections, such as temperature variation, strain, background stray fields, variation in the quadrupolar interaction, and instability in the applied bias magnetic field. Thus, this scheme yields a solid-state gyroscope with stability comparable to that achieved in atomic systems.

After the sensing sequence, the $^{14}$N spin is left in the state, $$|\psi_n\rangle = \frac{\sin(\Omega t)}{\sqrt{2}}(e^{+i\Omega t}|-1\rangle - e^{-i\Omega t}|+1\rangle) - \cos(\Omega t)|0\rangle \quad (3)$$

which can be mapped into a population difference between the NV levels thanks to the hyperfine coupling (here, one only considers the longitudinal component of the isotropic hyperfine interaction $AI_zS_z$ because of the large zero-field splitting $\Delta$).

The readout sequence, as shown in FIG. 2, with pulses on resonance to both $0 \leftrightarrow \pm 1$ transitions, generates the state, $$|\psi_{en}\rangle = \tfrac{1}{2}\sin(\Omega t)[e^{i\Omega t}(|-1,-1\rangle + |+1,-1\rangle) + e^{-i\Omega t}$$
$$(|+1,+1\rangle + |-1,+1\rangle) - \cos(\Omega t)|0,0\rangle] \qquad (4)$$

where $|m_z^S, m_z^I\rangle$ indicates an eigenstate of $S_z$ and $I_z$ for the electronic and nuclear spins, respectively. The time required to map the state onto the NV center is $t_{map}=230$ ns, which is close to the $T_2^*$ time for the NV at high densities, thus, one can expect a reduction in contrast. Indeed, it is the NV dephasing time that ultimately limits the allowed spin densities. A possible solution would be to perform a spin echo on both nuclear and electronic spins to extend the coherence time.

Optical readout extracts the information about the rotation $\Omega$. The measurement step can be repeated to improve the contrast. Although, at low field, the nuclear-spin relaxation time under optical illumination is relatively short, thus, limiting the number of repeated readouts when combined with a side-collection scheme giving high collection efficiency $\eta_m \approx 1$, one can still achieve a detection efficiency of $C \sim 0.25$ for $nr=100$ repetitions and a total readout time of $t_{ro} \approx 150$ μs. The higher detection efficiency will also allow a large dynamic range by exploiting adaptive phase-estimation schemes.

One can now consider the performance of the n-NV-gyroscope design with respect to sensitivity and stability and its potential advantages over competing technologies.

The sensitivity per unit time $\eta$ is ideally shot-noise limited: $\eta \propto 1/\sqrt{tN}$, where N is the number of nitrogen nuclear spins associated with NV centers in the diamond chip. The expected sensitivity can be estimated by limiting the interrogation time t to $T_2$ and taking into consideration the preparation and readout dead times $td=t_{pol}+t_{ro}$ and the detection efficiency C, $$\eta = \frac{\sqrt{T_2 + t_d}}{CT_2\sqrt{N}} \qquad (5)$$

Figure 3:
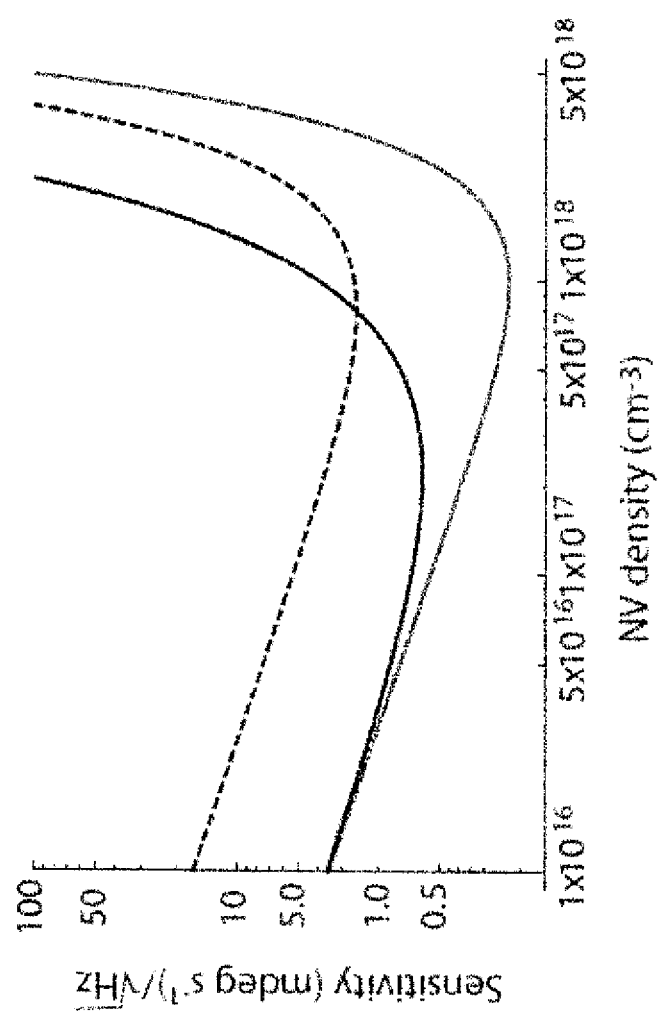
FIG. 3 is a graph illustrating an n-NV-gyroscope sensitivity

For a volume $V=1$ mm$^3$, containing $N=n-NVV/4 \approx 2.5 \times 10^{14}$ sensor spins along the rotation axis, the estimated sensitivity for the n-NV gyro is then $\eta \approx 0.5$ (mdegs$^{-1}$)/$\sqrt{Hz}$, better than the current MEMS gyroscopes, although in a slightly larger volume, as shown in FIG. 3.

Figure 4:
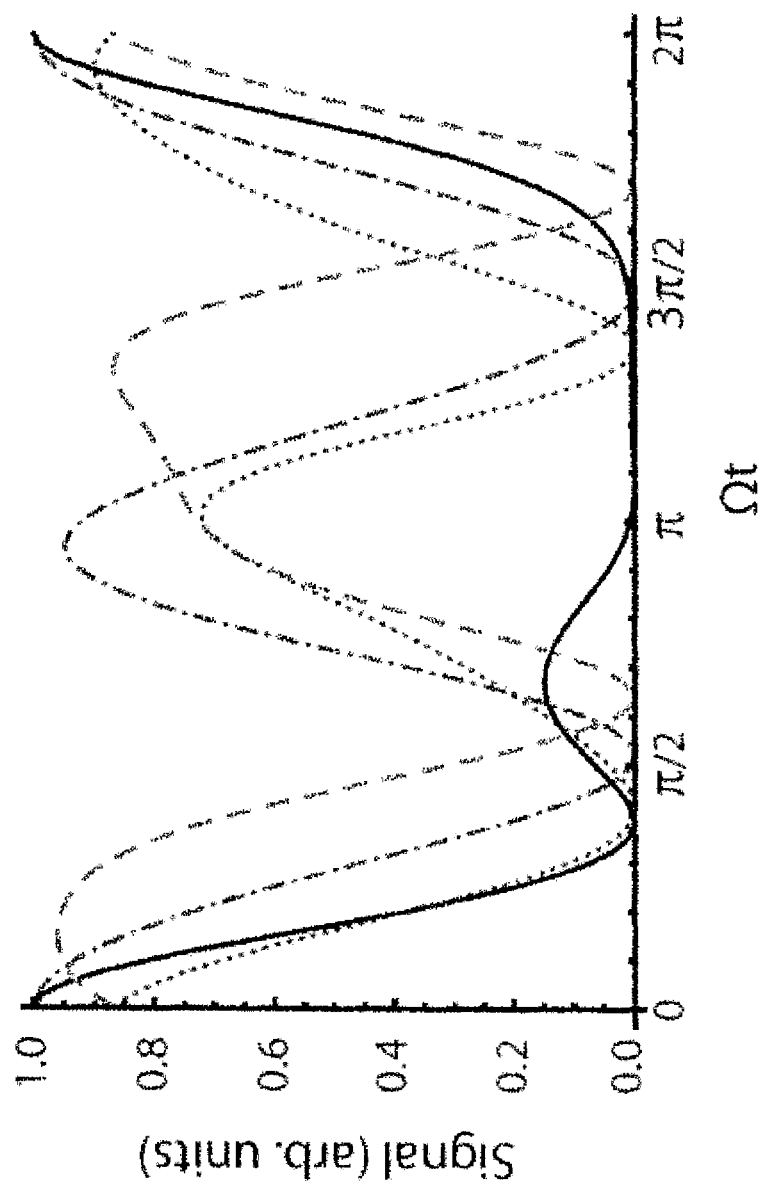
FIG. 4 is a graph illustrating the signal $S_c$ from the four classes of NV centers.

More importantly, the stability of the n-NV gyro can be much higher than for MEMS and can be comparable to atomic gyroscopes, shown in FIG. 4. Indeed, the echo-based scheme makes the n-NV gyro insensitive to drifts due to strain, temperature, and stray fields. In addition, the NV spin is a sensitive probe of these effects, capable of measuring magnetic and electric fields as well as frequency and temperature shifts. Because of almost 4 orders of magnitude larger sensitivity of the NV spin than the $^{14}$N spin (given by the ratio $\gamma_e/\gamma_N$), the NV can be used to monitor such drifts and to correct them via a feedback mechanism.

The NV center in diamond includes a substitutional nitrogen adjacent to a vacancy in the lattice. The nitrogen to-vacancy axis sets the direction of the electronic zero-field splitting and nuclear quadrupolar interaction. The axis can be along any of the four tetrahedral $\langle 1,1,1\rangle$ crystallographic directions of the diamond lattice. This intrinsic symmetry can be exploited to operate the n-NV gyro as a three-axis gyroscope, extracting information about the rotation rate as well as its direction.

Although the maximum sensitivity is achieved for rotations aligned with the symmetry axis, if the rotation is about an axis forming an angle $\{\theta,\phi\}$ with respect to the NV axis, the $^{14}$N still undergoes a complex evolution that depends on $\vec{\Omega}$. The two rf pulses in the Ramsey interferometry scheme differ not only by their phase $\psi_{1,2}$ in the NV x-y plane, but also by their flip angle $\alpha_{1,2}$. If one can assume the first pulse to be along the x axis for the first NV class, the second rf pulse is rotated by an angle $\psi_{1,2}=\psi(\theta,\phi,\Omega t)$ in the NV x-y plane with $$\tan(\Psi_2^1) = \frac{\sin^2(\theta)\sin(2\phi)\sin^2(\Omega t/2) + \cos(\theta)\sin(\Omega t)}{\cos(\Omega t) - \sin^2(\theta)\cos^2(\phi)\cos(\Omega t) + \sin^2(\theta)\cos^2(\phi)} \qquad (6)$$

The flip angle $\alpha_{1,2}=\alpha(\theta,\phi,\Omega t)$ is also reduced with respect to the nominal angle $\pi$, The state at the end of the Ramsey sequence is then given by $$|\psi_n\rangle = \frac{e^{i\psi_2}\left[\sin(\psi_2) - i\cos\left(\frac{\alpha_2}{2}\right)\cos(\psi_2)\right]}{\sqrt{2}}|+1\rangle - $$
$$\sin\left(\frac{\alpha_2}{2}\right)\cos(\psi_2)|0\rangle - \frac{e^{i\psi_2}\left[\sin(\psi_2) + i\cos\left(\frac{\alpha_2}{2}\right)\cos(\psi_2)\right]}{2}|-1\rangle \qquad (7)$$

from which one can extract information about the rotation rate $\Omega$. Similar expressions hold for the other NV classes if it is possible to drive excitation fields in the transverse plane of each family. Then, the angles $\alpha_2^c, \psi_2^c$ are different for each family of NVs, and measuring the signal from three families allows extracting information about $\vec{\Omega}$.

Assuming that the driving field is applied only along one direction for all the four NV classes, even the first excitation pulse angles $\{\psi_1^c, \alpha_1^c\}$ differ for each class, whereas, for the second pulse, $\{\psi_2^c, \alpha_2^c\}$ depend not only on the class, but also on the rotation vector $\vec{\Omega}$ via simple trigonometric relationships. The signal for each class is defined as, $$S^c = [\cos(\alpha_1^c/2)\cos(\alpha_2^c/2) - \sin(\alpha_1^c/2)\sin(\alpha_2^c/2)\cos$$
$$(\psi_1^c - \psi_2^c)]^2 \qquad (8)$$

which is shown in FIG. 4. The signal can be measured by sequentially mapping the nuclear-spin state onto the corresponding electronic spin via on resonance microwave pulses (a bias field of 10-20 G is sufficient to lift the frequency degeneracy among the four classes). A more efficient scheme would take advantage of repeated readouts and long relaxation times of the nuclear spins to measure the signal from three NV classes without the need to repeat the preparation and echo sequences. Although a driving field along a single direction makes the deconvolution algorithm more complex, the signal arising from three classes of NV centers is still enough to reconstruct the rotation rate and its direction.

The invention proposes a solid-state device able to measure rotation rates with a resolution of $\eta \approx 0.5$ (mdegs$^{-1}$)/$\sqrt{Hz}$ in a 1-mm$^3$ package while providing great stability. The device performance compares favorably with respect to other current. Even smaller devices—on the micron scale—could be useful by exploiting this long-time stability to improve the performance of the MEMS gyroscope in a combinatoric device, as shown in FIGS. 5A-5B.

In particular, FIG. 5A shows an integrated n-NVMEMS gyroscope 22, comprising a bulk acoustic wave (BAW) single-axis MEMS gyroscope 20 in an ~800-μm diamond disk 24 implanted with NV centers, whose nuclear spins form a spin gyroscope. The spins implanted in the disk are polarized by a laser 26. The electrodes 30 surrounding the disk 24 are silvered to allow for total internal reflection, and fluorescence is side collected by replacing one of them by an on-chip optical waveguide 32 at 638 nm. Strip lines 38 for rf or μw control are fabricated on the disk. FIG. 5B shows the operation of the BAW mechanical gyroscope 20. The BAW 20 is electrostatically driven in the second elliptic mode by a ~10-kHz sinusoidal signal from the drive electrodes 28.

A rotation out of the plane causes a decrease in the gap near the sense electrodes 36, leading to a capacitive measurement of the rotation. Combinatoric filtering with the n-NV measurement leads to noise rejection and improved stability. High-performance MEMS gyroscopes can be fabricated in diamond using reactive ion-etching tools. While the substrate itself acts as a mechanical gyroscope, the nuclear spins inside it act as a spin gyroscope. These two gyroscopes, employing complementary physical effects, are sensitive to different sources of noise, which can be corrected by Kalman-filter techniques. The integrated device would offer both stability and sensitivity in a small package.

The invention introduces a quantum sensor that provides a sensitive and stable three-axis gyroscope in the solid state. One can achieve high sensitivity by exploiting the long coherence time of the $^{14}$N nuclear spin associated with the nitrogen-vacancy center in diamond, combined with the efficient polarization and measurement of its electronic spin. Although the gyroscope is based on a simple Ramsey interferometry scheme, one can use coherent control of the quantum sensor to improve its coherence time and robustness against long-time drifts. Such a sensor can achieve a sensitivity of $\eta \sim 0.5$ (mdeg s$^{-1}$)/$\sqrt{\text{Hzmm}^3}$ while offering enhanced stability in a small footprint. In addition, we exploit the four axes of delocalization of the nitrogen-vacancy center to measure not only the rate of rotation, but also its direction, thus obtaining a compact three-axis gyroscope.

Although the present invention has been shown and described with respect to several preferred embodiments thereof, various changes, omissions and additions to the form and detail thereof, may be made therein, without departing from the spirit and scope of the invention.

What is claimed is:

1. An n-NV-based gyroscope comprising:
a diamond structure implanted with a plurality of NV centers, whose nuclear spins form a spin gyroscope; and
a plurality of radio-frequency (rf) coils and microwave (μw) co-planar waveguides being fabricated on the diamond structure to provide a sensitive and stable three-axis gyroscope in the solid state while achieving gyroscopic sensitivity by exploiting the coherence time of the $^{14}$N nuclear spin associated with the NV centers in the diamond structure combined with the efficient optical polarization and measurement of electronic spin.

2. The n-NV-based gyroscope of claim 1, wherein the gyroscopic sensitivity comprises 0.5 (mdeg s$^{-1}$)/$\sqrt{\text{Hzmm}^3}$.

3. The n-NV-based gyroscope of claim 1, wherein the stable three-axis gyroscope is based on a simple Ramsey interferometry scheme.

4. The n-NV-based gyroscope of claim 1, wherein the $^{14}$N nuclear spin is controlled via resonant radio frequency (rf) fields to perform a spin-echo based detection sequence.

5. The n-NV-based gyroscope of claim 1, wherein the NV centers comprise four axes of delocalization to measure not only the rate of rotation, but also the axis of the rotation, thus obtaining a compact three-axis gyroscope.

6. The n-NV-based gyroscope of claim 1, wherein the NV centers are polarized by a laser.

7. The n-NV-based gyroscope of claim 1, wherein the $^{14}$N nuclear spins are used as probes of the relative rotation between the diamond structure and one or more external rf-coils.

8. The n-NV-based gyroscope of claim 1, wherein the diamond structure is surrounded by a plurality of silvered electrodes to allow for total internal reflection and enhanced collection of the emitted fluorescent light.

9. The n-NV-based gyroscope of claim 1, wherein the $^{14}$N nuclear spin is initialized via longitudinally driven cross-polarization with the NV electronic spin.

10. The n-NV-based gyroscope of claim 1, wherein the $^{14}$N nuclear spin state, carrying information about the measured rotation, is mapped onto its respective electronic spin for efficient optical readout.

11. The n-NV-based gyroscope of claim 1, wherein the NV electronic spin is used to monitor drifts in temperature, magnetic and electric fields, strains and to correct them via a feedback mechanism.

12. A method of implementing a quantum sensor comprising:
implanting a plurality of NV centers in a diamond structure, whose nuclear spins form a spin gyroscope; and
fabricating a plurality of radio-frequency (rf) coils and microwave (μw) co-planar waveguides on the diamond structure to provide a sensitive and stable three-axis gyroscope in the solid state while achieving gyroscopic sensitivity by exploiting the coherence time of the $^{14}$N nuclear spin associated with the NV centers in the diamond structure combined with the efficient polarization and measurement of electronic spin of the co-planar waveguides.

13. The method of claim 12 wherein the gyroscopic sensitivity comprises 0.5 (mdeg s$^{-1}$)/$\sqrt{\text{Hzmm}^3}$.

14. The method of claim 12, wherein the stable three-axis gyroscope is based on a simple Ramsey interferometry scheme.

15. The method of claim 12, wherein the $^{14}$N nuclear spin is controlled via resonant radio frequency (rf) fields to perform a spin-echo based detection sequence.

16. The method of claim 12, wherein the NV centers comprise four axes of delocalization to measure not only the rate of rotation, but also direction of the axis of the rotation, thus obtaining a compact three-axis gyroscope.

17. The method of claim 12, wherein the NV centers are polarized by a laser.

18. The method of claim 12, wherein the $^{14}$N nuclear spins are used as probes of the relative rotation between the diamond structure and one or more external rf-coils.

19. The method of claim 12, wherein the diamond structure is surrounded by a plurality of silvered electrodes to allow for total internal reflection and enhanced collection of the emitted fluorescent light.

20. The method of claim 12, wherein the $^{14}$N nuclear spin is initialized via longitudinally driven cross-polarization with the NV electronic spin.

21. The method of claim 12, wherein the $^{14}$N nuclear state, carrying information about the measured rotation, is mapped onto its respective electronic spin for efficient optical readout.

22. The method of claim 12, wherein the NV electronic spin is used to monitor drifts in temperature, magnetic and electric fields, strains and to correct them via a feedback mechanism.

23. A quantum sensor comprising:
a diamond structure implanted with a plurality of NV centers, whose nuclear spins form a spin gyroscope; and
a plurality of radio-frequency (rf) coils and microwave (μw) co-planar waveguides being fabricated on the diamond structure to provide a sensitive and stable three-axis gyroscope in the solid state while achieving gyroscopic sensitivity by exploiting the coherence time of the $^{14}$N nuclear spin associated with the NV centers in the diamond structure combined with the efficient optical polarization and measurement of electronic spin.

24. The quantum sensor of claim 23, wherein the gyroscopic sensitivity comprises $0.5 \text{ (mdeg s}^{-1})/\sqrt{\text{Hz}}\text{mm}^3$.

25. The quantum sensor of claim 23, wherein the stable three-axis gyroscope is based on a simple Ramsey interferometry scheme.

26. The quantum sensor of claim 23, wherein the $^{14}$N nuclear spin is controlled via resonant radio frequency (rf) fields to perform a spin-echo based detection sequence.

27. The quantum sensor of claim 23, wherein the NV center comprise four axes of delocalization to measure not only the rate of rotation, but also direction of the axis of rotation, thus obtaining a compact three-axis gyroscope.

28. The quantum sensor of claim 23, wherein the NV centers are polarized by a laser.

29. The quantum sensor of claim 23, wherein the $^{14}$N nuclear spins are used as probes of the relative rotation between the diamond structure and one or more external rf-coils.

30. The quantum sensor of claim 23, wherein the diamond structure is surrounded by a plurality of silvered electrodes to allow for total internal reflection and enhanced collection of the emitted fluorescent light.

31. The quantum sensor of claim 23, wherein the $^{14}$N nuclear spin is initialized via longitudinally driven cross-polarization with the NV electronic spin.

32. The quantum sensor of claim 23, wherein the $^{14}$N nuclear spin state, carrying information about the measured rotation, is mapped onto its respective electronic spin for efficient optical readout.

33. The quantum sensor of claim 23, wherein the NV electronic spin is used to monitor drifts in temperature, magnetic and electric fields, strains and to correct them via a feedback mechanism.

* * * * *